(12) United States Patent
Zahiri

(10) Patent No.: US 6,962,572 B1
(45) Date of Patent: Nov. 8, 2005

(54) DYNAMIC LUMBAR BRACE

(76) Inventor: Hormoz Zahiri, 11718 Chenault St., Los Angeles, CA (US) 90049

( * ) Notice: Subject to any disclaimer, the term of this patent is extended or adjusted under 35 U.S.C. 154(b) by 0 days.

(21) Appl. No.: 10/870,655

(22) Filed: Jun. 16, 2004

(51) Int. Cl.$^7$ ................................................ A61F 5/00
(52) U.S. Cl. .......................... 602/19; 602/12; 602/32; 602/36; 128/869
(58) Field of Search .................... 602/5, 12, 19, 602/32, 36, 60, 61, 67; 2/464, 467, 466; 128/846, 128/869, 870, 873–876

(56) References Cited

U.S. PATENT DOCUMENTS

| | | | |
|---|---|---|---|
| 2,453,370 A * | 11/1948 | Hittenberger | 602/19 |
| 2,906,260 A * | 9/1959 | Myers | 602/19 |
| 3,095,875 A * | 7/1963 | Davidson et al. | 602/19 |
| 3,945,376 A * | 3/1976 | Kuehnegger | 602/19 |
| 4,285,336 A * | 8/1981 | Oebser et al. | 602/19 |
| 5,267,948 A * | 12/1993 | Elliott | 602/19 |
| 5,503,621 A * | 4/1996 | Miller | 602/19 |
| 5,599,287 A * | 2/1997 | Beczak et al. | 602/19 |
| 5,713,840 A * | 2/1998 | Brentham | 602/19 |
| 6,190,342 B1 * | 2/2001 | Taylor | 602/19 |
| 2003/0139694 A1 * | 7/2003 | Rugfelt et al. | 602/12 |
| 2004/0143204 A1 * | 7/2004 | Salmon et al. | 602/19 |

FOREIGN PATENT DOCUMENTS

| | | | | |
|---|---|---|---|---|
| GB | 2260270 A | * | 4/1993 | A61F 5/03 |

* cited by examiner

*Primary Examiner*—Henry Bennett
*Assistant Examiner*—Amanda Wieker
(74) *Attorney, Agent, or Firm*—Thomas I. Rozsa; Tony D. Chen

(57) ABSTRACT

A lumbar support brace which is designed to create a tightening effect to push the abdominal contents and abdomen toward the spinal column and as a result creates and increases the hydraulic pressure inside the abdomen and pushes the tissues against the spinal column and straightens the spinal column. In addition, a U-shaped member supports the spine on either side and is connected to a pelvic support member so that the abdomen, spine and pelvis are concurrently supported. The key feature of the present invention is that the support is a dynamic support which enables the wearer to engage in vigorously physical activity.

20 Claims, 1 Drawing Sheet

DYNAMIC LUMBAR BRACE

BACKGROUND OF THE INVENTION

1. Field of the Invention

The present invention generally relates to the field of lumbar support devices which provide support to the lower back to enable the wearer to engage in physical activities.

2. Description of the Prior Art

In general, all prior art braces of which the present inventor is aware provide some kind of support for maintaining or holding the lumbar spine in a specific position and all are immobilizers or binders. While these prior art devices provide support to help reduce back pain, they also substantially restrict movement.

Therefore, there is a significant need for an improved lumbar support which is flexible enough to enable the wearer to engage in both physical and athletic activity.

SUMMARY OF THE INVENTION

The present invention is a lumbar support brace which is designed to create a tightening effect to push the abdominal contents and abdominal wall toward the lumbar spinal column and as a result creates and increases the hydraulic pressure inside the abdomen and pushes the viserae and tissues against the spinal column and straightens the spinal column. In addition, a U-shaped member supports the spine on either side and is connected to a pelvic support member so that the abdomen, spine and pelvis are concurrently supported. The key feature of the present invention is that the support is a dynamic support which enables the wearer to engage in vigorously physical activity.

The invention is comprised of three major independent parts or components.

It has been discovered, according to the present invention, that if an abdominal plate which fits over the abdomen and is positioned between the pubic line and below the rib cage level is combined with a U-shaped thoracolumbar member which has a pair of parallel prongs located on both sides of the spinous processes of the lumbar spine extending from L1 vertebra below the thoracic spine down to the lumbar 5 vertebra just above the sacral bone, and is further combined with a pelvic ring controller which is generally triangular shape and fits over the sacral bone and over the corner of the pelvic bone on both sides, and if they are interconnected by flexible straps, then the abdomen is pushed against the spine and the combination supports the abdomen, lumbar spine and pelvis to provide a very dynamic flexible brace.

It has further been discovered, according to the present invention, that if the straps which interconnect the parts are flexible and adjustable by means of a belt buckle and mating opening on the straps or by hook and loop fasteners, then the device can be taut to fully support the abdomen, lumbar spine and pelvis.

It has also been discovered, according to the present invention, that if the U-shaped thoracolumbar member extends upwardly to between the shoulder blades, the spine can be even better supported so the wearer can engage in heavy physical labor. In such case, shoulder crossing straps pass over the shoulders from the U-shaped thoracolumbar member to the upper border of the abdominal plate to provide the necessary thoracic connection to the dynamic lumbar brace.

It is therefore an object of the present invention to provide a dynamic lumbar support to immobilize the spine so that the very lowest lumbar spine remains in a static position in a well balanced anatomical position and distributes the forces so as to permit the person to have maximum utilization of his body. In addition, the support is also provided to the trunk, lower limbs, and pelvis so that the person can have maximum utilization of these body parts.

It is a further object of the present invention to cause the stomach to be pushed towards and thereby straighten the spine while at the same time supporting the spine and the pelvis to provide firm yet flexible support so that the person can engage in a lot of activity such as engaging in tennis, raquetball, volleyball and basketball and similar sports.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
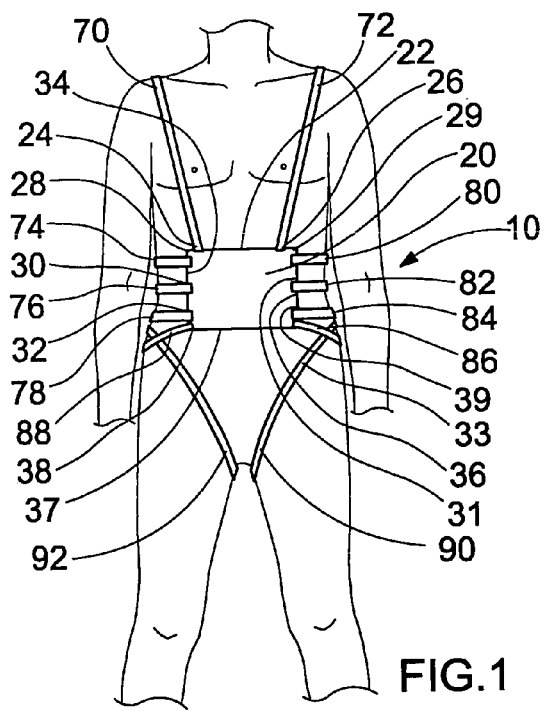
FIG. 1 is a front elevational view of the present invention in use by a wearer.
Figure 3:
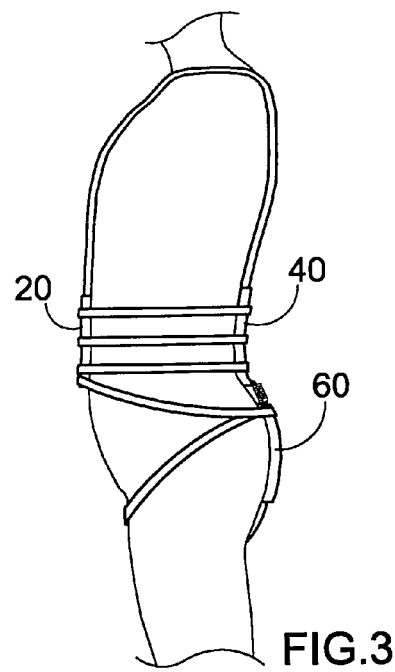
FIG. 3 is a side elevational view of the present invention in use by a wearer.
Figure 2:
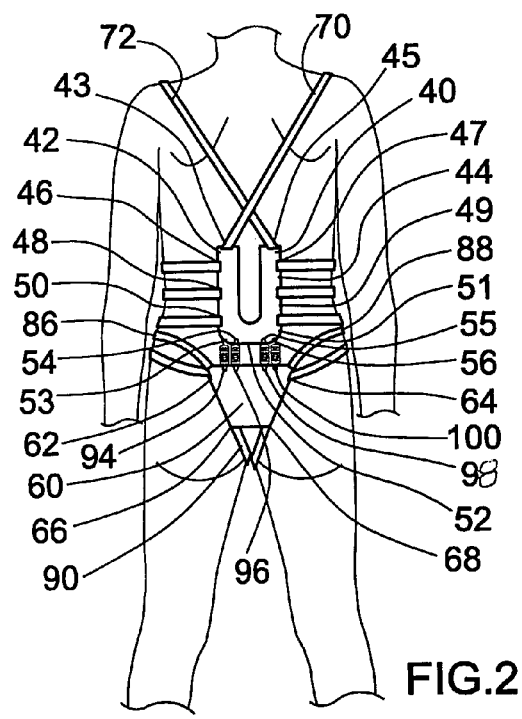
FIG. 2 is a rear elevational view of the present invention in use by a wearer.

The preferred embodiment of the present invention dynamic lumbar brace 10 is illustrated in FIGS. 1, 2 and 3. The purpose of the dynamic lumbar brace 10 is to immobilize the spine so that the lumbar spine remains in the static position but it is in a well balanced anatomical position and force distribution so as to permit the person to have maximum utilization of his body. The purpose of the dynamic lumbar brace is to support an athlete or a worker such as a housewife or any person who is engaged in repetitive or forceful flexion, extension, rotation, or tilting of the lumbar spine. Through use of the present invention dynamic lumbar brace 10, the brace allows all of the movements of the lumbar spine including flexion, extension, rotation or tilting to take place while it maintains and supports the normal alignment of the lumbar spine.

The dynamic lumbar brace 10 comprises three primary components, an abdominal plate 20, a U-shaped thoracolumbar member 40 and a pelvic ring controller 60. The abdominal plate 20 is illustrated in FIGS. 1 and 3 and the U-shaped thoracolumbar member 40 and pelvic ring controller 60 are illustrated in FIGS. 2 and 3. All three primary components will now be described.

The abdominal plate 20 is generally rectangular in shape as illustrated in FIG. 1 and abdominal plate 20 is a hard plate and is designed and sized to fit over the abdomen just above the pubic line. It does not place any pressure over the pubic bone. The abdominal plate 20 fits right in front of the stomach and covers the public bone over the navel and goes upwardly to just below the rib cage level. It terminates just below the rib cage level on the top 22. The abdominal plate 20 may be flared so that as the wearer engages in movements, the abdominal plate 20 will not interfere with the rib cage.

The abdominal plate 20 comprises two spaced apart top openings 24 and 26, three vertically spaced apart openings 28, 30 and 32 on one side 34 and three respectively parallel vertically spaced apart openings 29, 31 and 33 on the opposite side 36 and a first lower side opening 38 adjacent first side 34 and adjacent the lower edge 37 and a parallel second lower side opening 39 adjacent second side 36 and adjacent the lower edge 37.

The second major component of the dynamic lumbar brace 10 is the U-shaped thoracolumbar member 40 as illustrated in FIG. 2. The thoracolumbar member 40 is a sturdy U-shaped plate, made out of plastic or other strong body compatible material. The prongs 42 and 44 of the thoracolumbar member 40 extend upwardly as illustrated in FIG. 2 and are located on both sides of the spinous processes of the lumbar spine that are usually palpated under the skin in the midline and are extended from lumbar 5 vertebra just above the sacral bone up to the L1 vertebra below the thoracic spine.

The left prong 42 contains three vertically spaced apart openings 46, 48 and 50 and right prong 44 contains three respectively parallel vertically spaced apart openings 47, 49 and 51. The lower section 52 contains four spaced apart openings 53, 54, 55 and 56.

The third major component of the dynamic lumbar brace 10 is the pelvic ring controller 60. As illustrated in FIG. 2, the pelvic ring controller 60 is triangular in shape and is made of hard material such as plastic or other body compatible material which is soft enough to fit over the sacral bone and the corners of the pelvic bone. This is almost like an athletic support that is worn around the pelvic bone, around the abdominal and the lumbar spine. The pelvic ring controller 60 has a first upper opening 62, a second upper opening 64, a first lower opening 66 and a second lower opening 68.

All three components are connected together by means of a multiplicity of flexible and stretchable straps. The straps can be made of nylon or other flexible and stretchable material which can be opened and closed by mating fastening members such as hook and loop fasteners so that the straps can be tightened so that the three components of the dynamic lumbar brace are taut against the body. Such immobilization provides free or unrestricted movements between all three major components. However, the person must still feel comfortable.

The U-shaped thoracolumbar member and the pelvic ring controller are connected by two sets of springs, each set made or comprised of two springs and each set is located on either side of the spinous processes connecting the lower end of the U-shaped thoracocolumbar member to the superior border of the pelvic ring controller.

The upper portion 22 of the abdominal plate 20 and the upper ends of first prong 42 and second prong 44 of the thoracolumbar member 40 are connected by first shoulder strap 70 and second shoulder strap 72. As illustrated in FIGS. 1 and 2, the straps are worn like suspenders and are straight in front and crisscross on the back. First shoulder strap 70 extends over the wearer's right shoulder and is connected to opening 24 in abdominal plate 20 and to opening 43 in prong 42. Second shoulder strap 32 extends over the wearer's left shoulder and is connected to opening 26 in abdominal plate 20 and to opening 45 in prong 44.

The shoulder straps 70 and 72 connect the U-shaped thoracolumbar member 40 to the abdominal plate 20 passing over the shoulders and crossing in the back in order not to slide over the shoulders so they suspend these two elements. The straps 70 and 72 are adjustable.

Six side straps serve to connect the sides of the abdominal plate 20 to the prongs of the thoracolumbar member 40. First upper side strap 74 connects opening 28 in abdominal plate 20 to opening 47 in prong 44 of thoracolumbar member 40. First middle side strap 76 connects opening 30 in abdominal plate 20 to opening 49 in prong 44 of thoracolumbar member 40. First lower side strap 78 connects opening 32 in abdominal member 20 to opening 51 in prong 44 of thoracolumbar member 40. Second upper side strap 80 connects opening 29 in abdominal plate 20 to opening 46 in first prong 42 of thoracolumbar member 40. Second middle side strap 82 connects opening 31 in abdominal plate 20 to opening 48 in first prong 42 of thoracolumbar member 40. Second lower side strap 84 connects opening 33 in abdominal plate 20 to opening 50 in first prong 42 of thoracolumbar member 40.

Four pelvic straps are used to connect the pelvic ring controller 60. First upper pelvic strap 86 connects first upper opening 62 of the pelvic ring controller 60 to opening 39 of the abdominal plate 20. Second upper pelvic strap 88 connects the second upper opening 64 of the pelvic ring controller 60 to opening 38 of the abdominal plate. First lower pelvic strap 90 extends from first upper pelvic opening 62 across the front of the upper leg and to first lower pelvic opening 66. Second lower pelvic strap 92 extends from second upper pelvic opening 64 to second lower pelvic opening 68. These straps which keep the pelvic ring controller 60 in place are straps that start from the superior corner of the pelvic ring controller, pass through the anterior superior iliac crest of the pelvis and over the inguinal line coming to the perineal line and passing posteriorly connecting to the lower aspect of the pelvic ring controller.

The pelvic ring controller is made of plastic, sturdy but a little flexible. There is one piece in the back. It is a single piece that is on the back over the sacral bone and over the corner of the pelvic bones but then the rest of it are straps. So the straps cover like a belt around the pelvis and pass through the iliac crest and over the anatomical landmark of the anterior superior iliac crest. The straps on each side are split longitudinally to allow the bony prominence of the anterior superior iliac crest to fall into the opening. This design will decompress the bony prominence from undue pressure or contact irritation and will provide a superior holding quality as well as a better grasping of the pelvic ring with no chance for displacement of the straps or the pelvic ring controller component.

Finally, four springs 94, 96, 98 and 100 connect the lower section 52 of the thoracolumbar member 40 to the pelvic ring controller. First spring 94 connects opening 53 in the thoracolumbar member 40 to opening 61 in the pelvic ring controller. Second spring 90 connects opening 54 in the thoracolumbar member 40 to opening 63 in the pelvic ring controller 60. Third spring 98 connects opening 55 in the thoracolumbar member 40 to opening 65 in the pelvic ring controller. Forth spring 100 connects openings 56 in the thoracolumbar member 40 to opening 67 in the pelvic ring controller.

With straps 70, 72, 74, 76, 78, 80, 82 and 84 tightened, the abdominal plate 20 is tightened to the thoracolumbar member 40. This tightening effect will push the abdominal contents and abdomen toward the spinal column and as a result, creates and increases the hydraulic pressure inside the abdomen and pushes all the tissues against the spinal column and straightens the spinal column. The U-shaped thoracolumbar member 40 supports the spine on either side. Next the straps of the pelvic ring controller are tightened to control the pelvis. The straps 94, 96, 98, 100 are each about three inches long and are very strong.

Through the dynamic lumbar brace, the main joints are free to operate. The wearer can engage in athletic activities or heavy work or housework. The brace supports the back and spine and causes the stomach to be pushed against the back to give it greater strength. The hydraulic pressure in the abdomen created by the plate against the spine itself corrects the spine. The dynamic lumbar brace allows the user to do anything he wants without damaging his or her back or aggravating an existing lower back condition in any of the lower back motion segments.

The first and second lower pelvic straps 90 and 92 create the dynamic between all three components to really hold onto the lumbar spine while the springs are able to move around and allow the wearer to engage in all rotations and movements that are comprised of a combination of flexion, extension, rotation and tilting. The straps 90 and 92 go between the lower abdominal plate 20 and the upper part of the pelvic ring controller 60.

Figure 4:
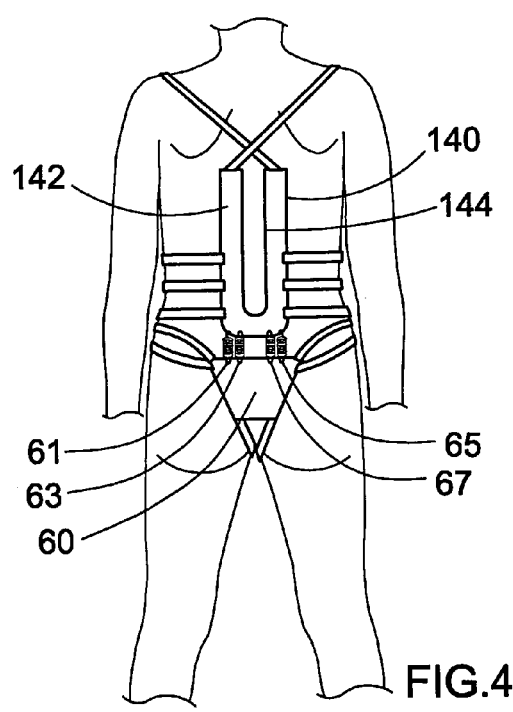
FIG. 4 is a rear elevational view of an alternative embodiment of the present invention in use by a wearer.

An alternative embodiment of the present invention is illustrated in FIG. 4. The abdominal plate 20 and the pelvic ring controller 60 and all of their component straps are the same as the first embodiment. The prongs 142 and 144 of the alternative embodiment thoracolumbar member 140 are modified in that the prongs 142 and 144 are much longer and extend to between the shoulder blades as illustrated in FIG. 4. The extended prongs 142 and 144 provide greater support on either side of the spine and enable the wearer to engage in heavy labor.

Each of the straps 70, 72, 74, 76, 78, 80, 82, 84, 86, 88, 90 and 92 can be made of flexible material such as neoprene, nylon etc. and can have conventional opening and closing means such as a belt buckle and corresponding openings, or mating hook and loop fasteners to that the straps can be tightened.

Each of the straps can be connected to each of the members as described by various connecting means such as clips instead of going through the openings as described.

Defined in detail, the present invention is a lumbar support for use by a wearer and to be used in conjunction with the wearer's abdomen, pubic bone, rib cage, spine, lumbar 5 vertebra just above the sacral bone, the L1 vertebra below the thoracic spine, the sacral bone, the pelvic bone, the anterior superior iliac crest of the pelvis, the inguinal line and the perineal line, the support comprising: (a) an abdominal plate of generally rectangular configuration and sized to be placed in front of the wearer's abdomen and which extends from the pubic bone over the navel and goes up to below the wearer's rib cage level; (b) a thoracolumbar member of U-shaped configuration with the prongs of the U-shaped configuration extending upwardly on the wearer, the thoracolumbar member configured so that the two prongs of the U-shape are located behind the wearer and extend on both sides of the spinous processes of the lumbar spine, the thoracolumbar member positioned to extend from the lumbar 5 vertebra just above the sacral bone of the wearer up to the L1 vertebra below the thoracic spine of the wearer; (c) a pelvic ring controller configured to rest against the backside of the wearer over the sacral bone and over the corner of the pelvic bone and positioned below the thoracolumbar member; (d) a multiplicity of flexible straps which interconnect an upper portion of an abdominal plate to an upper portion of the prongs of the thoracolumbar member; (e) a multiplicity of side straps which interconnect side portions of the abdominal plate to side portions of the prongs of the thoracolumbar member; (f) a multiplicity of springs which interconnect a lower portion of the thoracolumbar member to an upper portion of the pelvic ring controller; (g) a multiplicity of straps which interconnect an upper portion of the pelvic ring controller to a lower portion of the abdominal plate; and (h) a multiplicity of straps connecting upper and lower portions of the pelvic ring controller so that the straps pass through the anterior superior iliac crest of the pelvis and over the inguinal line coming to the perineal line and passing posteriorly; (i) whereby the straps are used to be tightened so that the abdomen is pushed toward the spine and the abdomen, spine and pelvis are supported during activity by the wearer.

Defined broadly, the present invention is a lumbar support for use by a wearer and to be used in conjunction with the wearer's abdomen, pubic bone, rib cage, spine, lumbar 5 vertebra just above the sacral bone, the wearer's shoulder blades, the sacral bone, the pelvic bone, the anterior superior iliac crest of the pelvis, the inguinal line and the perineal line, the support comprising: (a) an abdominal plate of generally rectangular configuration and sized to be placed in front of the wearer's abdomen and which extends from the pubic bone over the navel and goes up to below the wearer's rib cage level; (b) a thoracolumbar member of U-shaped configuration with the prongs of the U-shaped configuration extending upwardly on the wearer, the thoracolumbar member configured so that the two prongs of the U-shape are located behind the wearer and extend on both sides of the spinous processes of the lumbar spine, the thoracolumbar member positioned to extend from the lumbar 5 vertebra just above the sacral bone of the wearer up to between the wearer's shoulder blades; (c) a pelvic ring controller configured to rest against the backside of the wearer over the sacral bone and over the corner of the pelvic bone and positioned below the thoracolumbar member; (d) a multiplicity of flexible straps which interconnect an upper portion of an abdominal plate to an upper portion of the prongs of the thoracolumbar member; (e) a multiplicity of side straps which interconnect side portions of the abdominal plate to side portions of the prongs of the thoracolumbar member; (f) a multiplicity of springs which interconnect a lower portion of the thoracolumbar member to an upper portion of the pelvic ring controller; (g) a multiplicity of straps which interconnect an upper portion of the pelvic ring controller to a lower portion of the abdominal plate; and (h) a multiplicity of straps connecting upper and lower portions of the pelvic ring controller so that the straps pass through the anterior superior iliac crest of the pelvis and over the inguinal line coming to the perineal line and passing posteriorly; and (i) whereby the straps are used to be tightened so that the abdomen is pushed toward the spine and the abdomen, spine and pelvis are supported during activity by the wearer.

Defined more broadly, the present invention is a lumbar support for use by a wearer and to be used in conjunction with the wearer's abdomen, pubic bone, rib cage, spine, lumbar 5 vertebra just above the sacral bone, the L1 vertebra below the thoracic spine, the sacral bone, the pelvic bone, the anterior superior iliac crest of the pelvis, the inguinal line and the perineal line, the support comprising: (a) an abdominal plate sized to be placed in front of the wearer's abdomen and which extends from the pubic bone over the navel and goes up to below the wearer's rib cage level; (b) a thoracolumbar member of U-shaped configuration with the prongs of the U-shaped configuration extending upwardly on the wearer, the thoracolumbar member configured so that the two prongs of the U-shape are located behind the wearer and extend on both sides of the spinous processes of the lumbar spine, the thoracolumbar member positioned to extend from the lumbar 5 vertebra just above the sacral bone of the wearer up to the L1 vertebra below the thoracic spine of the wearer; (c) a pelvic ring controller configured to rest against the backside of the wearer over the sacral bone and over the corner of the pelvic bone and positioned below the thoracolumbar member; (d) flexible straps which interconnect an upper portion of an abdominal plate to an upper portion of the prongs of the thoracolumbar member; (e) at least one side strap on each side of the abdominal plate which respectively interconnect side portions of the abdominal plate to side portions of the prongs of the thoracolumbar member; (f) at least one spring which interconnects a lower portion of the thoracolumbar member to an upper portion of the pelvic ring controller; (g) at least one strap which interconnects an upper portion of the pelvic ring controller to a lower portion of the abdominal plate; and (h) at least one strap connecting upper and lower portions of the pelvic ring controller so that the at last one strap passes through the anterior superior iliac crest of the pelvis and over the inguinal line coming to the perineal line and passing posteriorly; (i) whereby the straps are used to be tightened so that the abdomen is pushed toward the spine and the abdomen, spine and pelvis are supported during activity by the wearer.

Defined even more broadly, the present invention is a support for use by a wearer and to be used in conjunction with the wearer's abdomen, pubic bone, rib cage, spine, lumbar 5 vertebra just above the sacral bone, the wearer's shoulder blades, the sacral bone, the pelvic bone, the anterior superior iliac crest of the pelvis, the inguinal line and the perineal line, the support comprising: (a) an abdominal plate sized to be placed in front of the wearer's abdomen and which extends from the pubic bone over the navel and goes up to below the wearer's rib cage level; (b) a thoracolumbar member of U-shaped configuration with the prongs of the U-shaped configuration extending upwardly on the wearer, the thoracolumbar member configured so that the two prongs of the U-shape are located behind the wearer and extend on both sides of the spinous processes of the lumbar spine, the thoracolumbar member positioned to extend from the lumbar 5 vertebra just above the sacral bone of the wearer up to between the wearer's shoulder blades; (c) a pelvic ring controller configured to rest against the backside of the wearer over the sacral bone and over the corner of the pelvic bone and positioned below the thoracolumbar member; (d) flexible straps which interconnect an upper portion of an abdominal plate to an upper portion of the prongs of the thoracolumbar member; (e) at least one strap on each side of the abdominal plate which respectively interconnect side portions of the abdominal plate to side portions of the prongs of the thoracolumbar member; (f) at least one spring which interconnects a lower portion of the thoracolumbar member to an upper portion of the pelvic ring controller; (g) at least one strap which interconnects an upper portion of the pelvic ring controller to a lower portion of the abdominal plate; and (h) at least one strap connecting upper and lower portions of the pelvic ring controller so that the at least one strap passes through the anterior superior iliac crest of the pelvis and over the inguinal line coming to the perineal line and passing posteriorly; (i) whereby the straps are used to be tightened so that the abdomen is pushed toward the spine and the abdomen, spine and pelvis are supported during activity by the wearer.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A lumbar support for use by a wearer and to be used in conjunction with the wearer's abdomen, pubic bone, rib cage, spine, lumbar 5 vertebra just above the sacral bone, the L1 vertebra below the thoracic spine, the sacral bone, the pelvic bone, the anterior superior iliac crest of the pelvis, the inguinal line and the perineal line, the support comprising:

a. an abdominal plate of generally rectangular configuration and sized to be placed in front of the wearer's abdomen and which is adapted to extend from the pubic bone over the navel and up to below the wearer's rib cage level;

b. a thoracolumbar member of U-shaped configuration with the prongs of the U-shaped configuration adapted to extend upwardly on the wearer, the thoracolumbar member configured so that the two prongs of the U-shape are located behind the wearer and are adapted to extend on both sides of the spinous processes of the lumbar spine, the thoracolumbar member adapted to be positioned to extend from the lumbar 5 vertebra just above the sacral bone of the wearer up to the L1 vertebra below the thoracic spine of the wearer;

c. a pelvic ring controller configured to rest against the backside of the wearer over the sacral bone and over the corner of the pelvic bone and positioned below the thoracolumbar member;

d. a multiplicity of flexible straps which interconnect an upper portion of an abdominal plate to an upper portion of said prongs of said thoracolumbar member;

e. a multiplicity of side straps which interconnect side portions of said abdominal plate to side portions of said prongs of said thoracolumbar member;

f. a multiplicity of springs which interconnect a lower portion of said thoracolumbar member to an upper portion of said pelvic ring controller;

g. a multiplicity of straps which interconnect an upper portion of said pelvic ring controller to a lower portion of said abdominal plate; and h. a multiplicity of straps connecting upper and lower portions of said pelvic ring controller so that the straps are adapted to pass through the anterior superior iliac crest of the pelvis and over the inguinal line coming to the perineal line and passing posteriorly;

i. whereby said straps are used to be tightened so that the abdomen is pushed toward the spine and the abdomen, spine and pelvis are supported during activity by the wearer.

2. A lumbar support in accordance with claim 1 wherein said abdominal plate is made of hard material.

3. A lumbar support in accordance with claim 2 wherein said hard material is plastic.

4. A lumbar support in accordance with claim 1 wherein said thoracolumbar member is made of hard material.

5. A lumbar support in accordance with claim 4 wherein said hard material is plastic.

6. A lumbar support in accordance with claim 1 wherein said pelvic ring controller is made of hard material.

7. A lumbar support in accordance with claim 6 wherein said hard material is plastic.

8. A lumbar support in accordance with claim 1 wherein each of said straps is made of flexible material.

9. A lumbar support in accordance with claim 1 wherein each of said straps has opening and closing means by which the straps can be tightened.

10. A lumbar support for use by a wearer and to be used in conjunction with the wearer's abdomen, pubic bone, rib cage, spine, lumbar 5 vertebra just above the sacral bone, the wearer's shoulder blades, the sacral bone, the pelvic bone, the anterior superior iliac crest of the pelvis, the inguinal line and the perineal line, the support comprising:
  a. an abdominal plate of generally rectangular configuration and sized to be placed in front of the wearer's abdomen and which is adapted to extend from the pubic bone over the navel and up to below the wearer's rib cage level;
  b. a thoracolumbar member of U-shaped configuration with the prongs of the U-shaped configuration adapted to extend upwardly on the wearer, the thoracolumbar member configured so that the two prongs of the U-shape are located behind the wearer and are adapted to extend on both sides of the spinous processes of the lumbar spine, the thoracolumbar member adapted to be positioned to extend from the lumbar 5 vertebra just above the sacral bone of the wearer up to between the wearer's shoulder blades;
  c. a pelvic ring controller configured to rest against the backside of the wearer over the sacral bone and over the corner of the pelvic bone and positioned below the thoracolumbar member;
  d. a multiplicity of flexible straps which interconnect an upper portion of an abdominal plate to an upper portion of said prongs of said thoracolumbar member;
  e. a multiplicity of side straps which interconnect side portions of said abdominal plate to side portions of said prongs of said thoracolumbar member;
  f. a multiplicity of springs which interconnect a lower portion of said thoracolumbar member to an upper portion of said pelvic ring controller;
  g. a multiplicity of straps which interconnect an upper portion of said pelvic ring controller to a lower portion of said abdominal plate; and
  h. a multiplicity of straps connecting upper and lower portions of said pelvic ring controller so that the straps are adapted to pass through the anterior superior iliac crest of the pelvis and over the inguinal line coming to the perineal line and passing posteriorly;
  i. whereby said straps are used to be tightened so that the abdomen is pushed toward the spine and the abdomen, spine and pelvis are supported during activity by the wearer.

11. A lumbar support in accordance with claim 10 wherein said abdominal plate is made of hard material.

12. A lumbar support in accordance with claim 11 wherein said hard material is plastic.

13. A lumbar support in accordance with claim 10 wherein said thoracolumbar member is made of hard material.

14. A lumbar support in accordance with claim 13 wherein said hard material is plastic.

15. A lumbar support in accordance with claim 10 wherein said pelvic ring controller is made of hard material.

16. A lumbar support in accordance with claim 15 wherein said hard material is plastic.

17. A lumbar support in accordance with claim 10 wherein each of said straps is made of flexible material.

18. A lumbar support in accordance with claim 10 wherein each of said straps has opening and closing means by which the straps can be tightened.

19. A lumbar support for use by a wearer and to be used in conjunction with the wearer's abdomen, pubic bone, rib cage, spine, lumbar 5 vertebra just above the sacral bone, the wearer's shoulder blades, the sacral bone, the pelvic bone, the anterior superior iliac crest of the pelvis, the inguinal line and the perineal line, the support comprising:
  a. an abdominal plate sized to be placed in front of the wearer's abdomen and which is adapted to extend from the pubic bone over the navel and up to below the wearer's rib cage level;
  b. a thoracolumbar member of U-shaped configuration with the prongs of the U-shaped configuration adapted to extend upwardly on the wearer, the thoracolumbar member configured so that the two prongs of the U-shape are located behind the wearer and are adapted to extend on both sides of the spinous processes of the lumbar spine, the thoracolumbar member adapted to be positioned to extend from the lumbar 5 vertebra just above the sacral bone of the wearer up to between the wearer's shoulder blades;
  c. a pelvic ring controller configured to rest against the backside of the wearer over the sacral bone and over the corner of the pelvic bone and positioned below the thoracolumbar member;
  d. flexible straps which interconnect an upper portion of an abdominal plate to an upper portion of said prongs of said thoracolumbar member;
  e. at least one strap on each side of said abdominal plate which respectively interconnect side portions of said abdominal plate to side portions of said prongs of said thoracolumbar member;
  f. at least one spring which interconnects a lower portion of said thoracolumbar member to an upper portion of said pelvic ring controller;
  g. at least one strap which interconnects an upper portion of said pelvic ring controller to a lower portion of said abdominal plate; and
  h. at least one strap connecting upper and lower portions of said pelvic ring controller so that the at least one strap passes is adapted to pass through the anterior superior iliac crest of the pelvis and over the inguinal line coming to the perineal line and passing posteriorly;
  i. whereby said straps are used to be tightened so that the abdomen is pushed toward h. the spine and the abdomen, spine and pelvis are supported during activity by the wearer.

20. A lumbar support for use by a wearer and to be used in conjunction with the wearer's abdomen, pubic bone, rib cage, spine, lumbar 5 vertebra just above the sacral bone, the wearer's shoulder blades, the sacral bone, the pelvic bone, the anterior superior iliac crest of the pelvis, the inguinal line and the perineal line, the support comprising:

a. an abdominal plate sized to be placed in front of the wearer's abdomen and which extends from the pubic bone over the navel and goes up to below the wearer's rib cage level;

b. a thoracolumbar member of U-shaped configuration with the prongs of the U-shaped configuration extending upwardly on the wearer, the thoracolumbar member configured so that the two prongs of the U-shape are located behind the wearer and extend on both sides of the spinous processes of the lumbar spine, the thoracolumbar member positioned to extend from the lumbar 5 vertebra just above the sacral bone of the wearer up to between the wearer's shoulder blades;

c. a pelvic ring controller configured to rest against the backside of the wearer over the sacral bone and over the corner of the pelvic bone and positioned below the thoracolumbar member;

d. flexible straps which interconnect an upper portion of an abdominal plate to an upper portion of said prongs of said thoracolumbar member;

e. at least one strap on each side of said abdominal plate which respectively interconnect side portions of said abdominal plate to side portions of said prongs of said thoracolumbar member;

f. at least one spring which interconnects a lower portion of said thoracolumbar member to an upper portion of said pelvic ring controller;

g. at least one strap which interconnects an upper portion of said pelvic ring controller to a lower portion of said abdominal plate; and h. at least one strap connecting upper and lower portions of said pelvic ring controller so that the at least one strap passes through the anterior superior iliac crest of the pelvis and over the inguinal line coming to the perineal line and passing posteriorly;

i. whereby said straps are used to be tightened so that the abdomen is pushed toward the spine and the abdomen, spine and pelvis are supported during activity by the wearer.

\* \* \* \* \*